United States Patent
Mizutani

(10) Patent No.: US 9,714,917 B2
(45) Date of Patent: Jul. 25, 2017

(54) METHOD OF CONTROLLING LAMBDA SENSOR PREHEATING AND LAMBDA SENSOR DRIVE CONTROLLER

(71) Applicant: Bosch Corporation, Tokyo (JP)

(72) Inventor: Hiroyuki Mizutani, Kanagawa (JP)

(73) Assignee: Bosch Corporation, Tokyo (JP)

( * ) Notice: Subject to any disclaimer, the term of this patent is extended or adjusted under 35 U.S.C. 154(b) by 48 days.

(21) Appl. No.: 14/769,300

(22) PCT Filed: Feb. 13, 2014

(86) PCT No.: PCT/JP2014/053305
§ 371 (c)(1),
(2) Date: Aug. 20, 2015

(87) PCT Pub. No.: WO2014/132804
PCT Pub. Date: Sep. 4, 2014

(65) Prior Publication Data
US 2015/0377827 A1 Dec. 31, 2015

(30) Foreign Application Priority Data
Feb. 27, 2013 (JP) .................. 2013-037567

(51) Int. Cl.
*G01N 27/409* (2006.01)
*G01N 27/416* (2006.01)
(Continued)

(52) U.S. Cl.
CPC ..... *G01N 27/4163* (2013.01); *F02D 41/1494* (2013.01); *G01N 27/409* (2013.01);
(Continued)

(58) Field of Classification Search
CPC .............. G01N 27/4067; G01N 27/409; F02D 41/1494; F02D 41/1454; F02D 2041/2027; F02N 2300/108
See application file for complete search history.

(56) References Cited

U.S. PATENT DOCUMENTS 9,458,784 B2 * 10/2016 Uemura .............. F02D 41/1454
2005/0241361 A1 11/2005 Smith

FOREIGN PATENT DOCUMENTS

DE  102012214717 A1  2/2014
DE  102013221980 A1  10/2014
(Continued)

OTHER PUBLICATIONS

International Search Report for Application No. PCT/JP2014/053305 dated May 20, 2014 (English Translation, 2 pages).

*Primary Examiner* — Blake A Tankersley
(74) *Attorney, Agent, or Firm* — Michael Best & Friedrich LLP

(57) ABSTRACT

A desired effective voltage can be ensured with certainty in a preheating control. An operation control part 52 reads a correction value c with respect to a battery voltage Vb at the time of performing correction based on preliminarily stored correlation between a battery voltage Vb of a vehicle-use battery and a correction value c (S104, S106), and compensates for lowering of an effective value of a pulse voltage by adding a correction value c to a duty ratio calculated by a predetermined arithmetic expression thus ensuring a desired effective voltage with certainty in a preheating control.

10 Claims, 5 Drawing Sheets

(51) Int. Cl.
  *G01N 27/406* (2006.01)
  *F02D 41/14* (2006.01)
  *G01N 27/419* (2006.01)
  *G01N 33/00* (2006.01)
  *F02D 41/20* (2006.01)

(52) U.S. Cl.
  CPC ....... *G01N 27/4067* (2013.01); *G01N 27/419* (2013.01); *G01N 33/0036* (2013.01); *F02D 2041/2027* (2013.01); *F02D 2200/503* (2013.01); *F02N 2300/108* (2013.01)

(56) References Cited

FOREIGN PATENT DOCUMENTS

| | | |
|---|---|---|
| JP | 200493386 | 3/2004 |
| JP | 2007225560 | 9/2007 |
| JP | 2008232961 | 10/2008 |
| JP | 2009288082 | 12/2009 |
| JP | 2009294006 | 12/2009 |

\* cited by examiner

S102: INITIALIZE WHEN TIME tdr ELAPSES FROM STARTING ENGINE

S104: MEASURE Vb

S106: READ CORRECTION VALUE

S108: CALCULATE PREHEATING DUTY RATIO

S110: tdr>PREHEATING TIME?

S112: USUAL DUTY RATIO CALCULATION

S202: INITIALIZE WHEN TIME tdr ELAPSES FROM STARTING ENGINE

S204: MEASURE Vb

S206: MEASURE ECU TEMPERATURE

S208: DETERMINE CORRECTION MAP AND READ CORRECTION VALUE

S210: CALCULATE PREHEATING DUTY RATIO

S212: tdr>PREHEATING TIME?

S214: USUAL DUTY RATIO CALCULATION

S302: INITIALIZE WHEN TIME tdr ELAPSES FROM STARTING ENGINE

S304: READ SHIPPING DATA

S306: DETERMINE CORRECTION MAP BASED ON SHIPPING DATA

S308: MEASURE Vb

S310: MEASURE ECU TEMPERATURE

S312: DETERMINE CORRECTION MAP AND READ CORRECTION VALUE

S314: CALCULATE PREHEATING DUTY RATIO

S316: tdr>PREHEATING TIME?

S318: USUAL DUTY RATIO CALCULATION

METHOD OF CONTROLLING LAMBDA SENSOR PREHEATING AND LAMBDA SENSOR DRIVE CONTROLLER

BACKGROUND OF THE INVENTION

The present invention relates to a lambda oxygen sensor for detecting concentration of oxygen in an exhaust gas from a vehicle or the like, and more particularly to a lambda oxygen sensor with which the enhancement of reliability of a preheating control and the like can be acquired.

In a lambda oxygen sensor where it is necessary to maintain a temperature of a sensor element at an active temperature, it is necessary to perform a preheating control of a heater before performing an operation of detecting concentration of oxygen. Various control methods and devices have been proposed and put into practice aiming at the enhancement of reliability, stability and the like of such a preheating control.

For example, there have been disclosed techniques including a technique where correlation between a heater resistance value and a temperature is focused, the heater resistance value is detected, and it is determined whether or not a temperature of the whole sensor arrives at a sufficient temperature for performing a detection operation based on the resistance value (see JP-A-2009-288082 and the like, for example).

The supply of electricity to a heater for a lambda oxygen sensor often adopts a method where a pulse voltage having a predetermined pulse width is applied to the heater at a predetermined repetition cycle. In such a method, a pulse width is determined based on a premise that a pulse voltage waveform is a square shape. In an actual operation, however, a delay occurs in a rise time or a fall time of a pulse because of a delay of a signal in a drive circuit, an electric characteristic of a semiconductor element or the like.

Accordingly, an effective voltage which a voltage to be applied to the heater is required to be cannot be maintained thus giving rise to a possibility that shortage or excess of preheating is brought about.

SUMMARY OF THE INVENTION

However, as in the case of the prior art described previously, with only the determination of whether or not a heater temperature is appropriate based solely on the detection of a heater resistance value, it is impossible to determine whether or not a prescribed effective voltage is ensured. Accordingly, there exists a drawback that it is difficult to perform a preheating control without bringing about shortage or excess of preheating while maintaining a required effective voltage with certainty. Further, it is necessary for a lambda oxygen sensor to eliminate extra moisture at the time of performing preheating with certainty. Accordingly, when preheating is finished without ensuring sufficient preheating at an original effective voltage and a state of the lambda oxygen sensor is shifted to a usual heating state, there is a possibility that a lifetime of the lambda oxygen sensor will be adversely affected by such heating. Further, there also exists a drawback that excessively large preheating also adversely affects the lifetime of the lambda oxygen sensor.

The invention has been made in view of the above-mentioned circumstances, and it is an object of the invention to provide a lambda oxygen sensor preheating control method and a lambda oxygen sensor drive control device which can realize a highly reliable preheating control by ensuring a desired effective voltage in a preheating control with certainty.

To achieve the above-mentioned object of the invention, there is provided a lambda oxygen sensor preheating control method using a lambda oxygen sensor preheating control device which is configured to preheat an inner heater for a lambda oxygen sensor by applying a pulse voltage generated by a PWM control to the internal heater, wherein a correction is performed to a duty ratio of the pulse voltage determined based on a predetermined arithmetic expression so as to compensate for lowering of an effective value of the pulse voltage at the duty ratio caused by a delay of a rise time or a fall time generated in the pulse voltage.

Further, to achieve the above-mentioned object of the invention, there is provided a lambda oxygen sensor drive control device which includes: an operation control part which generates and outputs a control signal for controlling the supply of electricity to an internal heater for a lambda oxygen sensor; and an energization drive part which supplies electricity to the internal heater by applying a pulse voltage generated by a PWM control to the internal heater based on a control signal from the operation control part, wherein the operation control part is configured to perform a correction to a duty ratio of the pulse voltage determined based on a predetermined arithmetic expression so as to compensate for lowering of an effective value of the pulse voltage at the duty ratio caused by a delay of a rise time or a fall time generated in the pulse voltage.

According to the invention, electricity can be supplied to the internal heater while setting an effective value of a pulse voltage to be applied to the internal heater as close as possible to an original value and hence, the invention can acquire an advantageous effect that a reliable and stable preheating control can be realized without bringing about shortage or excess of preheating.

Particularly, when it is inevitable that the lambda oxygen sensor be driven at a small duty ratio, an adverse influence caused by lowering of an effective value of a pulse voltage is large in many cases. According to the invention, however, a more reliable and stable preheating control can be realized by suppressing with certainty such lowering of the effective value.

DETAILED DESCRIPTION

Figure 1:
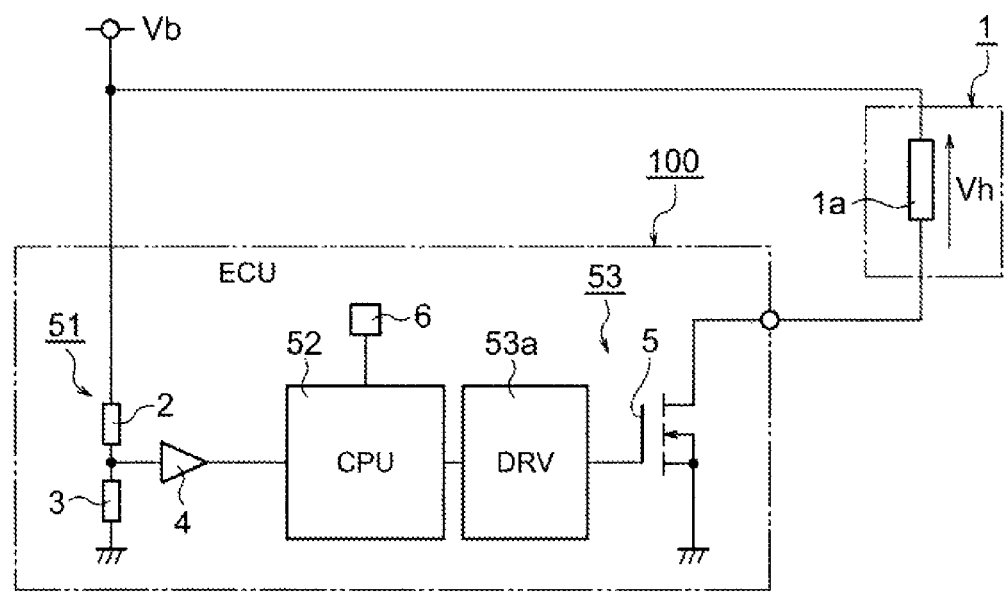
FIG. 1 is a constitutional view showing a constitutional example of a lambda oxygen sensor drive control device according to an embodiment of the invention.

Hereinafter, an embodiment of the invention is explained by reference to FIG. 1 to FIG. 6.

In the explanation made hereinafter, members, the arrangement of the members and the like do not limit the invention, and the members, the arrangement of the members and the like may be modified without departing from the gist of the invention.

Firstly, the constitution of the lambda oxygen sensor drive control device according to the embodiment of the invention is explained by reference to FIG. 1.

The lambda oxygen sensor drive control device according to the embodiment of the invention is formed of an electronic control unit (in FIG. 1, expressed as "ECU") 100 which controls an operation of a vehicle. The electronic control unit 100 includes: a battery voltage detection part 51; an operation control part (in FIG. 1, expressed as "CPU") 52; and an energization drive part 53 as main constitutional elements.

The battery voltage detection part 51 detects a voltage of a vehicle-use battery (not shown in the drawing) and supplies a detection voltage to the operation control part 52. The battery voltage detection part 51 according to the embodiment of the invention includes: first and second detection resistors 2, 3 which are connected in series between a vehicle-use battery not shown in the drawing and a ground; and a buffer amplifier 4 as main constitutional elements.

A node between the first detection resistor 2 and the second detection resistor 3 is connected to an input stage of the buffer amplifier 4, a divided voltage corresponding to a voltage Vb of the vehicle-use battery is inputted to the operation control part 52 via the buffer amplifier 4, and is used for performing the lambda oxygen sensor drive control processing and the like in the operation control part 52.

The operation control part 52 includes, besides a microcomputer (not shown in the drawing) or an ASIC (Application Specific Integrated Circuit) having the known/well-known constitution as main components thereof, for example, memory elements such as a RAM and a ROM (not shown in the drawing), an interface circuit (not shown in the drawing) for outputting a control signal to the energization drive part 53 and the like.

The operation control part 52, as described later, executes the lambda oxygen sensor drive control processing or the like such as the calculation of a duty ratio of a pulse voltage to be applied to the lambda oxygen sensor 1.

The energization drive part 53 includes: a drive circuit (in FIG. 1, expressed as "DRV") 53a; and an energization control semiconductor element 5. When the energization control semiconductor element 5 is driven and controlled by the drive circuit 53a based on a control signal from the operation control part 52, an energization control of an internal heater 1a of the lambda oxygen sensor 1 is performed.

As the energization control semiconductor element 5, a MOS FET or the like is used, for example. A drain of the energization control semiconductor element 5 is connected to one end of the internal heater 1a of the lambda oxygen sensor 1, a source of the energization control semiconductor element 5 is connected to the ground, and a gate of the energization control semiconductor element 5 is connected to an output stage of the drive circuit 53a. Further, a battery voltage Vb of a vehicle-use battery (not shown in the drawing) is applied to the other end of the internal heater 1a.

Due to such a constitution, the conduction or the non-conduction of the energization control semiconductor element 5 is controlled in response to a gate voltage which constitutes a control signal applied to the energization control semiconductor element 5 from the drive circuit 53a, and along with such a control, the energization of the internal heater 1a can be controlled.

To be more specific, the lambda oxygen sensor 1 is a wide band lambda oxygen sensor or the like, for example.

As is generally well-known, the lambda oxygen sensor 1 includes the internal heater 1a. The internal heater 1a preheats the lambda oxygen sensor 1 before the lambda oxygen sensor 1 receives a detection signal so as to enable the lambda oxygen sensor 1 to obtain a stable detection signal.

In FIG. 1, the illustration of an output part which outputs a detection signal corresponding to an oxygen concentration detected by the lambda oxygen sensor 1 is omitted in the drawing.

In a second embodiment described later, the explanation is made on a premise that a temperature sensor 6 is arranged at a suitable position in the inside of the electronic control unit 100. A detection signal of the temperature sensor 6 is inputted to the operation control part 52 as a signal indicative of a temperature in the inside of the electronic control unit 100, and is used for performing the lambda oxygen sensor preheating control processing or the like in the second embodiment after being converted into a digital signal.

Next, the first embodiment of the lambda oxygen sensor preheating control processing according to the embodiment of the invention performed by the above-mentioned operation control part 52 is explained by reference to the subroutine flowchart shown in FIG. 2.

Figure 2:
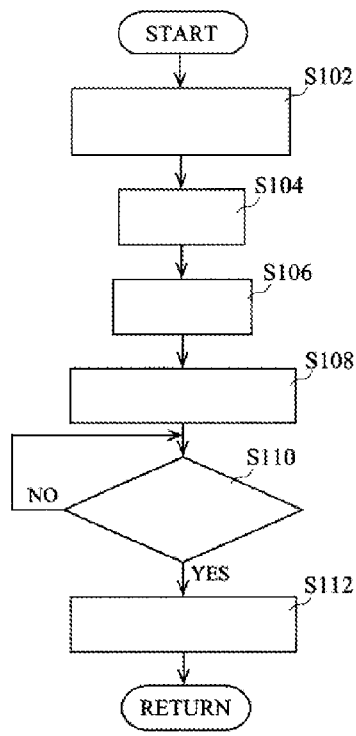
FIG. 2 is a subroutine flowchart showing processing steps in a first embodiment of a lambda oxygen sensor preheating control method according to the embodiment of the invention which is applied to the lambda oxygen sensor drive control device shown in FIG. 1.

Firstly, the subroutine flowchart shown in FIG. 2 shows one subroutine processing which is performed together with an energization drive control of the lambda oxygen sensor 1 which is performed by the operation control part 52 in the substantially same manner as the prior art.

Further, the series of processing shown in FIG. 2 is performed on a premise that the series of processing is started along with the starting of the vehicle-use engine (not shown in the drawing).

When processing is started by the operation control part 52, firstly, a tdr which is a variable expressing a time elapsed from starting a vehicle-use engine (not shown in the drawing) is initialized to zero (see step S102 in FIG. 2). In the operation control part 52, the execution of a so-called time measuring program which is conventionally well-known is started from the starting of the vehicle-use engine, and an elapsed time from the starting of the vehicle-use engine is measured.

Next, a battery voltage Vb of the vehicle-use battery not shown in the drawing is measured (see step S104 in FIG. 2). Although a voltage drop in the second detecting resistor 3 which is detected by the battery voltage detection part 51 is inputted to the operation control part 52, the voltage is proportional to the battery voltage Vb. Accordingly, the battery voltage Vb is calculated based on a voltage drop of the second detecting resistor 3 by the operation control part 52.

Next, a correction value for correcting a duty ratio of a pulse voltage applied to the internal heater 1a is read from a battery voltage correction value map (not shown in the drawing) expressing the correlation between a battery voltage and a correction value which is preliminarily stored in a suitable storage region of the operation control part 52 based on a battery voltage Vb (see step S106 in FIG. 2).

Firstly, with respect to the energization of the internal heater 1a, in the same manner as the prior art, a pulse voltage is applied to the internal heater 1a at a predetermined repetition cycle by controlling turning on and off of the energization control semiconductor element 5 by the operation control part 52 via the drive circuit 53a, and the energization control of the internal heater 1a is performed by a so-called PWM control.

Here, a pulse width of a pulse voltage is determined based on a duty ratio Dc which is calculated by the following expression 1 in the lambda oxygen sensor drive control processing which is separately performed in the operation control part 52 in the same manner as the prior art.

$$Dc=[(Vheff\_tar)^2 \times 100]/Vb^2 \qquad \text{expression 1}$$

The duty ratio Dc is a value obtained by expressing a ratio of a pulse width with respect to a repetition cycle T of a pulse by a percentage.

Vheff_tar is a target effective voltage obtained by expressing a target voltage at both ends of the internal heater 1a in terms of an effective value, and Vb is an actual value (actual battery voltage) of a battery voltage obtained by executing processing in step S104.

A duty ratio Dc may be obtained using a following expression 2 described below where $(Vheff\_tar)^2 \times 100$ in the above-mentioned expression 1 is replaced with $(Vb\_nom)^2 \times Dc\_nom$ which is a simplified form of $(Vheff\_tar)^2 \times 100$. Here, Vb_nom is a nominal value of a battery voltage of a vehicle-use battery (not shown in the drawing), and Dc_nom is a duty ratio necessary for preheating the internal heater 1a in the case where the internal heater 1a, the energization control semiconductor element 5, the drive circuit 53 and the like possess characteristics as designed, and a battery voltage Vb is a normal value. For the sake of convenience, such a duty ratio is referred to as a "heater reference drive ON duty ratio".

$$Dc=[(Vb\_nom)^2]/Vb^2 \times Dc\_nom \qquad \text{expression 2}$$

The above-mentioned duty ratio is a value which is supposed to be set for obtaining a target effective voltage Vheff_tar on a premise that a pulse voltage waveform is a rectangular waveform. When the pulse voltage waveform is a rectangular waveform, a rise time and a fall time are supposed to be zero originally. However, in case of an actual pulse voltage waveform, the actual pulse voltage waveform is influenced by delay in turning on and off of various semiconductor elements in the drive circuit 53a and electric characteristics of the semiconductor elements and hence, rising and falling take time to some extent. Accordingly, so-called rounding of a waveform occurs in a rise waveform and a fall waveform and hence, a required duty ratio Dc becomes substantially small whereby the sufficient duty ratio Dc cannot be ensured.

Inventors of the invention have found that, as a result of their extensive studies, the larger a battery voltage Vb of the vehicle-use battery becomes, the more the decrease in a duty ratio Dc becomes conspicuous. The inventors of the invention have made further extensive studies based on such finding, and as a result of such extensive studies, the inventors have arrived at the conclusion that by adding a correction term to the expression 1 corresponding to a battery voltage Vb, it is possible to compensate for a change in duty ratio Dc by being influenced by an actual battery voltage Vb. To be more specific, it is possible to compensate for the lowering of a target effective voltage Vheff_tar.

That is, it is preferable to perform the correction of a duty ratio Dc expressed by the following expression 3.

$$Dc=[(Vheff\_tar)^2 \times 100]/Vb^2 + c(Vb) \qquad \text{expression 3}$$

In the expression 3, c(Vb) is a correction term and means that a correction value c is expressed as a function of a battery voltage Vb.

In the embodiment of the invention, appropriate correction values c for various battery voltages Vb are determined based on tests, simulation results and the like, and maps (battery voltage correction value maps) which are prepared in such a manner that battery voltages Vb are used as input parameters, and correction values c corresponding to inputted battery voltages Vb are readable are preliminarily stored and held in a suitable storage region in the operation control part 52.

In step S106, a correction value c corresponding to a battery voltage Vb obtained in processing in step S104 is read from a battery voltage correction value map which is preliminarily stored in the operation control part 52.

Next, a duty ratio Dc for preheating energization is calculated (see step S108 in FIG. 2).

That is, a duty ratio Dc corrected based on the above-mentioned expression 3 is calculated, and the energization control semiconductor element 5 is driven at the corrected duty ratio Dc so that preheating of the internal heater 1a is performed.

Next, it is determined whether or not an elapsed time tdr from starting of the engine exceeds a preset preheating period (see step S110 in FIG. 2). When it is determined that the elapsed time tdr does not exceed the preheating period (when the determination in step S110 is negative), preheating of the internal heater 1a is continued. On the other hand, when it is determined that the elapsed time tdr exceeds the preheating period (when the determination in step S110 is affirmative), preheating is finished, and the duty ratio Dc is returned to a normal value based on a separately prepared calculation expression (see step S112 in FIG. 2), and the series of processing is finished. Then, processing returns to a main routine not shown in the drawing.

According to the embodiment of the invention, a duty ratio Dc is corrected as described above and hence, the invention can realize the preheating control which does not bring about the shortage of preheating. Further, the correction of a duty ratio Dc is performed with certainty as described above, that is, accurately without excess or shortage of preheating. For example, by setting a correction term as a function of a battery voltage as in the case of the embodiment of the invention, compared to the case where a correction term is merely a constant, it is possible to avoid a situation where a duty ratio is excessively corrected so that preheating becomes excessively large. Accordingly, the invention can reduce with certainty an adverse effect exerted on a lifetime of the lambda oxygen sensor by excessive preheating.

Next, a second embodiment is explained by reference to a sub routine flowchart shown in FIG. 3.

The second embodiment is provided on a premise that a temperature sensor 6 is provided in the inside of an electronic control unit 100.

In the second embodiment, processing in steps S202, S204 are respectively basically the same as processing in steps S102, S104 in the first embodiment shown in FIG. 2. Accordingly, the repeated detailed explanation of the processing is omitted here, and the explanation of the processing in the second embodiment starts from the processing in step S206.

In step S206, a temperature in the electronic control unit 100 (hereinafter referred to as "ECU temperature") is measured. That is, a detection signal of the temperature sensor 6 is read by the operation control part 52, and is temporarily stored and held in a suitable memory region.

Figure 3:
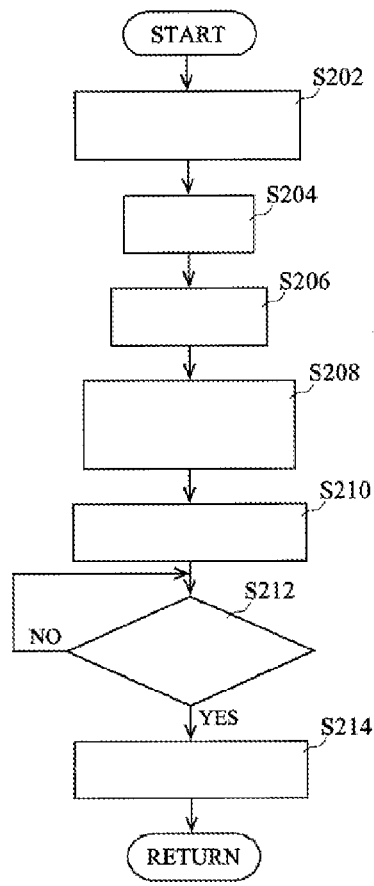
FIG. 3 is a subroutine flowchart showing processing steps in a second embodiment of the lambda oxygen sensor preheating control method according to the embodiment of the invention which is applied to the lambda oxygen sensor drive control device shown in FIG. 1.

Next, the determination of a battery voltage-correction value map and reading of a correction value in accordance with the map are performed (see step S208 in FIG. 3).

That is, in this embodiment, in the same manner as the first embodiment explained by reference to FIG. 2 previously, lambda oxygen sensor preheating control processing of this embodiment also uses the battery voltage-correction value map. However, the battery voltage-correction value map in the first embodiment described previously is prepared on a premise that a temperature in the inside of the electronic control unit 100 is a standard temperature (for example, 24° C.).

On the other hand, in the second embodiment, in view of a fact that a correction value c with respect to a battery voltage Vb changes depending on an ECU temperature, particularly, a temperature environment where an energization control semiconductor element 5 is disposed in a strict sense, battery voltage-correction value maps at various ECU temperatures are prepared based on results of tests and simulations or the like, the battery voltage-correction value maps are stored preliminarily in a suitable memory region of the operation control part 52, and a battery voltage-correction value map corresponding to an ECU temperature acquired in step S206 is selectable.

Figure 5:
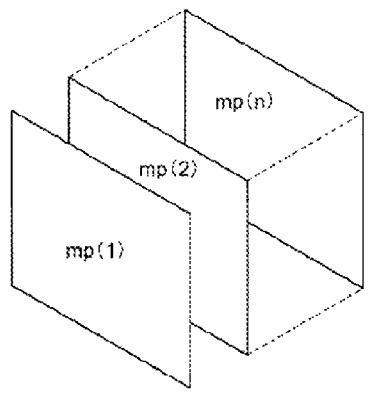
FIG. 5 is an explanatory view schematically showing a case where a battery voltage/correction value map is provided for every ECU temperature.

FIG. 5 is an explanatory view schematically showing a plurality of battery voltage-correction value maps stored in the operation control part 52. To explain this drawing, firstly, in the drawing, symbols mp(1) to mp(n) indicate a plurality of battery voltage-correction value maps prepared for respective ECU temperatures. That is, the respective maps mp (1) to mp (n) differ from each other in ECU temperature which is a premise of the respective maps. For example, the map mp (1) is configured to read correction values c with respect to various battery voltages Vb when an ECU temperature is t1, and the map mp (2) is configured to read correction values c with respect to various battery voltages Vb when the ECU temperature is t2. With respect to temperatures between the temperature t1 and the temperature t2, it is preferable to arithmetically calculate a correction values c using a so-called interpolation.

When a battery voltage-correction value map corresponding to an ECU temperature is selected, a correction value corresponding to a battery voltage Vb measured in step S204 is read. In this respect, this processing is basically the same as the processing in step S106 described previously by reference to FIG. 2.

Next, a duty ratio Dc for preheating energization is calculated (see step 210 in FIG. 3).

Processing ranging from step S210 to step S214 inclusive have basically the same processing contents as steps S108, S110, S112 shown in FIG. 2 respectively. Accordingly, the repeated explanation of the processing is omitted here.

In this manner, in the second embodiment, the battery voltage-correction value maps corresponding to various ECU temperatures are prepared, and a duty ratio Dc is calculated using a correction value which conforms to an ECU temperature. Accordingly, compared to the first embodiment, in the second embodiment, a duty ratio Dc can be corrected more properly and hence, preheating of an inner heater 1a can be performed more properly.

Accordingly, it is possible to avoid with more certainty the occurrence of a state where although the correction is performed, the correction is performed excessively so that preheating is performed excessively. As a result, it is possible to reduce with more certainty an adverse effect exerted on a lifetime of a lambda oxygen sensor by excessive preheating.

Next, a third embodiment is explained by reference to a subroutine flowchart shown in FIG. 4.

A rate of dependency of correction values of a battery voltage-correction value map on an individual electric characteristic of an energization control semiconductor element 5 is high. In view of this fact, in the third embodiment, for every plurality of energization control semiconductor elements to be used or for every group out of groups formed by dividing a plurality of energization control semiconductor elements to be used (dividing the plurality of energization control semiconductor elements to be used based on manufacturing lots, for example), battery voltage-correction value maps with respect to various ECU temperatures are preliminarily prepared for the respective groups based on actual measured data, the battery voltage-correction value maps are stored in an operation control part 52, and any one of the battery voltage-correction value maps is selectively used as described later.

The third embodiment is, in the same manner as the second embodiment described previously, provided on a premise that a temperature sensor 6 is disposed in the inside of an electronic control unit 100.

Figure 4:
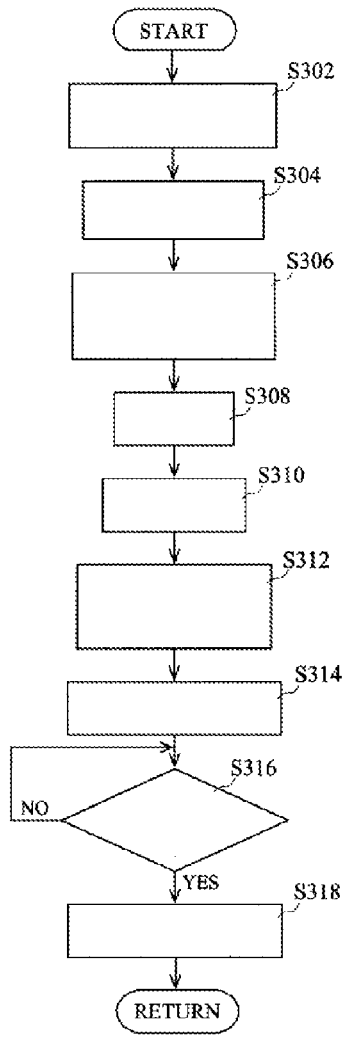
FIG. 4 is a subroutine flowchart showing processing steps in a third embodiment of the lambda oxygen sensor preheating control method according to the embodiment of the invention which is applied to the lambda oxygen sensor drive control device shown in FIG. 1.

When processing is started by an operation control part 52, firstly, tdr which is a variable expressing a time elapsed from starting a vehicle engine (not shown in the drawing) is initialized to zero (see step S302 in FIG. 4). Since this processing in step S302 is basically the same as the processing in step S102 shown in FIG. 2, the detailed explanation of the processing is omitted here.

Next, reading of shipping data of the energization control semiconductor elements 5 is performed (see step S304 in FIG. 4).

That is, in the third embodiment, to select a battery voltage-correction value maps (described in detail later), identification numbers or identification symbols (hereinafter referred to as "shipping data" for the sake of convenience of explanation) which are preliminarily determined for specifying the energization control semiconductor elements 5 or shipping data which are preliminarily determined for specifying which groups the energization control semiconductor elements 5 belong to are stored and held in a suitable memory region of the operation control part 52. In this step S304, reading of the shipping data is performed.

Next, using the read shipping data as an index, one group is determined from a plurality of groups of battery voltage-correction value maps preliminarily stored in the operation control part 52 (see step S306 in FIG. 4).

Figure 6:
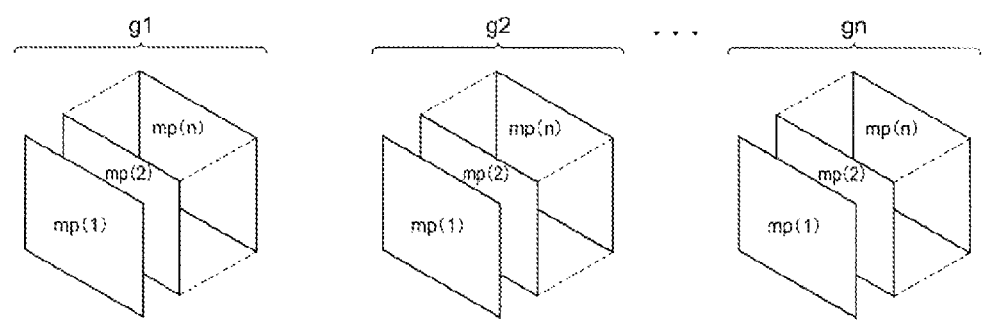
FIG. 6 is an explanatory view for schematically showing a case where the battery voltage/correction value map provided for every ECU temperature is provided for every energization control semiconductor element.

FIG. 6 schematically shows a constitutional example of battery voltage-correction value maps preliminarily stored in the operation control part 52. Hereinafter, the battery voltage-correction value maps in the third embodiment are explained by reference to FIG. 6.

Firstly, in FIG. 6, in the same manner as in the example explained by reference to FIG. 5 previously, symbols mp (1) to mp (n) indicate battery voltage-correction value maps corresponding to various ECU temperatures.

In FIG. 6, symbols g1 to gn are identification symbols expressing groups.

For example, assume a case where there are n pieces of energization control semiconductor elements used in the manufacture of a lambda oxygen sensor drive control device, battery voltage-correction value maps corresponding to various ECU temperatures are prepared based on actual measured data for individual energization control semiconductor elements, and the battery voltage-correction value maps are stored in the operation control part 52. In this case, symbols g1 to gn are identification numbers or identification symbols per se dividing n pieces of energization control semiconductor elements or the numbers which are determined separately corresponding to these identification numbers or identification symbols.

Accordingly, the battery voltage-correction value maps in each group g1 to gn are, when the energization control semiconductor elements corresponding to the battery voltage-correction value maps are used respectively, battery voltage-correction value maps where the battery voltage-correction value maps corresponding to various ECU temperatures are prepared based on actual measured data.

Instead of providing a plurality of battery voltage-correction value maps corresponding to various ECU temperatures for respective individual energization control semiconductor elements as described above, it is also preferable that energization control semiconductor elements be divided into a plurality of groups g1 to gn using electric characteristics or the like of the energization control semiconductor elements as indexes, and a plurality of battery voltage-correction value maps corresponding to a plurality of energization control semiconductor elements be provided for each group.

That is, in this case, it is preferable that the battery voltage-correction value maps in each group g1 to gn be set such that each correction value is determined as a standard value for the plurality of energization control semiconductor elements belonging to the group as will be described next.

For example, it is preferable that the battery voltage-correction value maps be prepared based on data actually measured when electricity is supplied to the inner heater 1a using the energization control semiconductor element having a standard electric characteristic out of the plurality of energization control semiconductor elements belonging to the group.

Further, instead of the above-mentioned battery voltage-correction value maps based on the energization control semiconductor element having the standard electric characteristic, it is preferable to adopt battery voltage-correction value maps where the battery voltage-correction value maps are obtained based on actual measured data with respect to a plurality of respective energization control semiconductor elements included in the same group, an average value, a root mean square value or the like is calculated with respect to correction values obtained based on the respective battery voltage-correction value maps, and a result of the calculation is set as a correction value.

With respect to grouping of energization control semiconductor elements, besides the above-mentioned grouping, for example, when the energization control semiconductor elements to be used are divided into a plurality of so-called manufacture lots, the energization control semiconductor elements are divided for respective manufacture lots.

Returning to the explanation of FIG. 4, after the battery voltage-correction value maps are determined as described above, the measurement of a battery voltage Vb of a vehicle-use battery (not shown in the drawings) is performed (see step S308 in FIG. 4).

Processing ranging from step S308 to step S318 inclusive are basically equal to the processing in steps S204 to S214 inclusive shown in FIG. 3 respectively. Accordingly, the repeated detailed explanation of the respective processing is omitted here.

Next, a fourth embodiment is explained.

The fourth embodiment is, in the same manner as the third embodiment described previously, provided on a premise that a temperature sensor 6 is disposed in the inside of an electronic control unit 100.

Firstly, in the third embodiment described previously, with respect to a plurality of energization control semiconductors to be used, battery voltage-correction value maps are prepared based on actual measured data respectively. Alternatively, with respect to a plurality of energization control semiconductor elements to be used, for example, the energization control semiconductor elements are divided into groups based on manufacturing lots or the like, and battery voltage-correction value maps which become standards of the respective groups are prepared based on actual measured data with respect to the respective groups. Then, the battery voltage-correction value maps are preliminarily stored in a suitable memory region of the operation control part 52. When the energization control semiconductor elements to be used are specified for respective vehicles, numbers or the like for identifying the energization control semiconductor elements are stored in the operation control part 52. When the vehicle is used, the battery voltage-correction value maps corresponding to the identification numbers or the like are selected from the stored identification numbers or the like of the energization control semiconductor elements, and the battery voltage-correction value maps are used in the correction of a duty ratio.

On the other hand, in the fourth embodiment, when energization control semiconductor elements to be used are specified for respective vehicles, battery voltage-correction value maps suitable for a case where such specified energization control semiconductor elements are used are prepared based on actual measured data, the battery voltage-correction value maps are stored in a suitable memory region of the operation control part 52, and the battery voltage-correction value maps are used in the correction of a duty ratio.

Accordingly, with respect to processing step performed by the operation control part 52, unlike the third embodiment, the battery voltage-correction value maps to be used as described above are suitable for the energization control semiconductor elements preliminarily specified. Accordingly, the processing steps of the fourth embodiment are same as the processing steps of the second embodiment shown in FIG. 3 basically except for a point where the selection of the group based on shipping data (see steps S304, S306 shown in FIG. 4) becomes unnecessary. Therefore, the repeated explanation of the contents of respective processing is omitted.

In the embodiments of the invention, the explanation has been made with respect to the case where battery voltage-correction value maps used in setting a value of a correction term of a duty ratio Dc correspond to ECU temperatures and the case where the battery voltage-correction value maps correspond to characteristics of individual energization control semiconductor elements or characteristics of groups of energization control semiconductor elements besides the ECU temperatures. However, the invention is not limited to these cases, and it is needless to say that various modifications can be added within the scope of the invention. For example, the case where the battery voltage-correction value maps used in setting a correction value of a correction term of a duty ratio correspond to characteristics of individual energization control semiconductor elements, but do not correspond to ECU temperatures also fall within the scope of the invention.

The invention is suitably applicable to a vehicle or the like where a preheating control of a lambda oxygen sensor with high reliability and high stability is desirable.

The invention claimed is:

1. A lambda oxygen sensor preheating control method using a lambda oxygen sensor preheating control device, the method comprising:
    preheating an internal heater for a lambda oxygen sensor by applying a pulse voltage generated by a PWM control to the internal heater; and
    applying a correction to a duty ratio of the pulse voltage by the lambda oxygen sensor preheating control device based on a predetermined arithmetic expression so as to compensate for lowering of an effective value of the pulse voltage at the duty ratio caused by a delay of a rise time or a fall time of the generated pulse voltage.

2. The lambda oxygen sensor preheating control method according to claim 1, wherein the correction is performed by adding a correction term to the duty ratio calculated by the predetermined arithmetic expression, and the correction term is a correction value determined with respect to a battery voltage of a vehicle-use battery at the time of performing the correction based on a correlation between the battery voltage and the correction value.

3. The lambda oxygen sensor preheating control method according to claim 2, wherein a plurality of correlations between the battery voltages of the vehicle-use battery and the correction values are determined corresponding to temperatures in the vicinity of a semiconductor element used for controlling the supply of electricity to the internal heater, and the correlation is selected based on a temperature in the vicinity of the semiconductor element.

4. The lambda oxygen sensor preheating control method according to claim 3, further comprising:
    determining the plurality of correlations between the battery voltages of the vehicle-use battery and correction values corresponding to the temperatures in the vicinity of a semiconductor element used for controlling the supply of electricity to the internal heater based on actual measured data for each of a plurality of semiconductor element used,
    storing the plurality of correlations for each of the plurality of semiconductor elements,
    providing data identifying a semiconductor element being used in a vehicle, and
    selecting the correlation for the semiconductor element being used from the stored plurality of correlations.

5. The lambda oxygen sensor preheating control method according to claim 3, further comprising:
    dividing the plurality of correlations into a plurality of groups,
    assigning each of a plurality of semiconductor elements to one of the plurality of groups, and
    selecting the correlations associated with the one of the plurality of groups to which the semiconductor element being used is assigned from the plurality of correlations.

6. A lambda oxygen sensor drive control device comprising:
    an operation controller which generates and outputs a control signal for controlling the supply of electricity to an internal heater for a lambda oxygen sensor; and
    an energization driver which supplies electricity to the internal heater by applying a pulse voltage generated by a PWM control to the internal heater based on a control signal from the operation controller,
    wherein the operation controller is configured to perform a correction to a duty ratio of the pulse voltage determined based on a predetermined arithmetic expression so as to compensate for a lowering of an effective value of the pulse voltage at the duty ratio caused by a delay of a rise time or a fall time generated in the pulse voltage.

7. The lambda oxygen sensor drive control device according to claim 6, wherein the operation controller is configured to perform the correction by adding a correction term to the duty ratio calculated by the predetermined arithmetic expression, and is configured to obtain a correction value determined with respect to a battery voltage of a vehicle-use battery at the time of performing the correction based on previously stored correlations between the battery voltages and the correction values as the correction term.

8. The lambda oxygen sensor drive control device according to claim 7, wherein a plurality of correlations between the battery voltages of the vehicle-use battery and the correction values are determined corresponding to temperatures in the vicinity of a semiconductor element used for controlling the supply of electricity to the internal heater, and the operation controller is configured to select the correlation based on a temperature in the vicinity of the semiconductor element.

9. The lambda oxygen sensor drive control device according to claim 8, wherein a plurality of correlations between battery voltages of the vehicle-use battery and correction values corresponding to the temperatures in the vicinity of the semiconductor element used for controlling the supply of electricity to the internal heater based on actual measured data for every semiconductor elements to be used are determined and stored,
    and
    the operation controller is configured to use the correlation for the semiconductor element used in performing the correction.

10. The lambda oxygen sensor drive control device according to claim 8, wherein the plurality of correlations are divided into groups,
    each of a plurality of semiconductor elements are assigned to one of the plurality of groups, and
    the operation controller is configured to select the correlations associated with the one of the plurality of groups to which the semiconductor element being used is assigned from the plurality of correlations.

* * * * *